United States Patent [19]

Romeo et al.

[11] Patent Number: 5,350,841
[45] Date of Patent: Sep. 27, 1994

[54] GANGLIOSIDE DERIVATIVES

[75] Inventors: Aurelio Romeo, Rome; Gino Toffano; Alberta Leon, both of Padova, all of Italy

[73] Assignee: Fidia S.p.A., Abano Terme, Italy

[21] Appl. No.: 922,383

[22] Filed: Jul. 31, 1992

[30] Foreign Application Priority Data

Aug. 1, 1991 [IT] Italy .................. PD91A000139

[51] Int. Cl.$^5$ .............. A61K 31/70; C12P 19/04; C07H 5/06
[52] U.S. Cl. ........................ 536/53; 435/84; 435/101; 536/55; 536/55.1; 536/55.3
[58] Field of Search ............ 536/53, 55, 55.1, 55.3; 514/54, 25; 435/101, 84

[56] References Cited

U.S. PATENT DOCUMENTS 4,713,374 12/1987 Della Valle et al. .
4,849,413 7/1989 Valle .................... 514/53

FOREIGN PATENT DOCUMENTS 0373039 6/1990 European Pat. Off. .
0410881 1/1991 European Pat. Off. .
0410883 1/1991 European Pat. Off. .

*Primary Examiner*—Herbert J. Lilling
*Attorney, Agent, or Firm*—Birch, Stewart, Kolasch & Birch

[57] ABSTRACT

Novel ganglioside derivatives comprised of a basic natural or semisynthetic ganglioside, in which the carboxyl group in the sialic part of the natural or semisynthetic ganglioside is converted into a carboxylamide with an aliphatic amino acid with a carboxylic or sulfonic acid function, and salts thereof are prepared. The semisynthetic ganglioside components can be chosen from the group consisting of N-acyl-N-lyso-gangliosides, N'-acyl-N'-lyso-gangliosides and N,N'-diacyl-N,N'-di-lyso-gangliosides, wherein "acyl" designates a moiety of an optionally substituted aliphatic acid. The ganglioside derivatives can be used in pharmaceutical preparations to be used in nervous system pathologies.

44 Claims, No Drawings

GANGLIOSIDE DERIVATIVES

BACKGROUND AND FIELD OF THE INVENTION

The present invention relates to certain novel ganglioside derivatives and more exactly to ganglioside derivatives comprised of a basic natural or semisynthetic ganglioside, in which the carboxyl group in the sialic part of said natural or semisynthetic ganglioside is converted into a carboxylamide with an aliphatic amino acid with a carboxylic or sulfonic acid function, and salts thereof. The semisynthetic ganglioside components can be chosen from the group consisting of N-acyl-N-lyso-gangliosides, N'-acyl-N'-lyso-gangliosides and N,N'-diacyl-N,N'-di-lyso-gangliosides wherein the N-acyl and N'-acyl groups are identical or different and each is a moiety of an optionally substituted aliphatic acid. The invention also relates to pharmaceutical preparations containing said compounds as active ingredients, and the therapeutic use of the new products and of the corresponding pharmaceutical preparations.

TECHNICAL BACKGROUND

Some ganglioside amides have already been described in the literature, for example in the U.S. Pat. No. 4,713,374 issued 15.12.1987: their neuronotrophic action is better than that of gangliosides which manifests itself as a prolonged activity. The neuronotrophic properties of these compounds and of gangliosides and of their aforesaid semisynthetic derivatives, the effect of which is to stimulate "sprouting" of nerve cells and consequently nerve function recovery, render said compounds useful as drugs in various therapies for the treatment of nervous system pathologies, in particular of the peripheral and central nervous systems, and their application can be recommended in peripheral nervous system pathologies of traumatic, compressive, degenerative, metabolic or toxic-infective origin, wherein nervous regeneration and neuromuscular function recovery must be stimulated, and in central nervous system pathologies of a traumatic, anoxic, degenerative or toxic-infective origin wherein neuronal phenomena for functional recovery must be stimulated.

It is also well known that gangliosides, for example the ganglioside $GM_1$, also possess an anti-neuronotoxic activity, that is, they are able to limit neurotoxicity induced by excitatory amino acids (EAA) which can result in severe damage to the central nervous system if it becomes sufficiently intense (J. W. Olney: Excitotoxic amino acids and neuropsychiatric disorders—Ann. Rev. Pharmacol. Toxicol. 30, 47-71, 1990). Acute cerebral damage can have various causes, but whatever its origin the outcome is neuronal damage with the consequent death of some neurons. The damaged neurons may die not only during and/or immediately after damage (primary neuronal death) but also later (secondary neuronal death).

Secondary neurodegeneration is mediated by the overexcitement of excitatory amino acid receptors, the activation of which unleashes a cascade of cellular events ($Ca^{+2}$-dependent enzyme activation, $Ca^{+2}$ flow, second messenger activation etc.), the result of which is neuronal death. The surviving neurons are able to operate neuroplastic repair phenomena, the expression of which is regulated by neuronotrophic factors (NTF). Thanks to gangliosides' twofold mechanism (neuronotrophic and antineuronotoxic effects), they are virtually able to limit not only long-term degenerative phenomena, such as those mentioned above, but also to limit and/or prevent EAA-induced neurotoxicity, and therefore to combat possible damage resulting from said diseases.

BRIEF DESCRIPTION OF THE INVENTION

The novel amides of the present invention possess these two mechanisms in a particularly favorable manner, having a far more intense neuronotrophic activity than gangliosides and their known esters or amides, and an anti-neuronotoxic effect reaching and exceeding the upper limit of that of gangliosides themselves and their functional derivatives. The new compounds are therefore very suitable as drugs for the treatment of said conditions.

DETAILED DESCRIPTION OF THE INVENTION

The starting (basic) ganglioside compounds for the preparation of amides according to the present invention can be:

1) natural gangliosides such as those obtained by extraction from tissues and organs of the nervous system;

2) semisynthetic ganglioside derivatives wherein the amino groups of the ceramide and/or neuraminic parts of natural gangliosides have been deacylated and one or both of said amino groups are reacylated with acyl moieties from pure aliphatic acids, optionally substituted as explained below.

Group 1) includes the various products obtained by extraction and described in the literature, which products are generally mixtures of chemical compounds, especially with regard to the ceramide part, which comprises, as is known, various higher aliphatic acids. Thus, the starting gangliosides can be those wherein the oligosaccharide is formed by a maximum of 4 hexose or N-acetylhexosamine residues, but with at least one hexose residue present, and wherein this saccharide moiety is chemically unitary. The hexoses are preferably chosen from the group formed by glucose and galactose and N-acetylhexoseamines from the group formed by N-acetylglucosamine and N-acetylgalactoseamine. The number of sialic groups present may be 1, 2, 3, 4 or 5, the sialic acids being preferably N-acetylneuraminic and N-glycolylneuraminic acid. The sialic acids may be acylated at one of the hydroxyl groups present in their structures, for example at the hydroxyl group in position 8, if this is not already occupied by a ketose bond which binds it to another sialic acid residue. The ceramide moiety may vary in the length of the carbon atom chain of the sphingosines, which may vary between 12 and 22 carbon atoms, and in the length of its acyl residue, which may also be within this range. Apart from this, the ceramide residue may vary due to the presence or absence of the double bond in the sphingosine and generally this residue is largely composed of unsaturated N-acylated-sphingosine and a low percentage of the corresponding saturated compound. One particularly important group of gangliosides contains double-bond sphingosines in the ceramide residue, acylated with 18 or 20 carbon atoms in their chain, and corresponding saturated compounds, while their saturated or unsaturated acyl group, unsubstituted or substituted by hydroxyls, also has the same number of 18 or 20 carbon atoms.

The gangliosides of this group are for example those extracted from vertebrate brains, such as those described in the article "Gangliosides of the Nervous System" in "Glycolipid Methodology", Lloyd A. Witting Ed., American Oil Chemists Society, Champaign, III 187, 214) (1976) (see in particular plate 1), for example gangliosides $GM_4$, $GM_3$, $GM_2$, $GM_1$-Glc NAc, $GD_2$, $GD_{1a}$-GalNAc, $GT_{1c}$, GQ, $GT_1$ (group A) and in particular the following gangliosides (group B):

$GM_1$
Gal(1→3)GalNAC(1→4)Gal(1→4)Glc(1→1)Ceramide

NANA $GD_{1a}$
Gal(1→3)GalNAC(1→4)Gal(1→4)Glc(1→1)Ceramide

 

NANA    NANA $GD_{1b}$
Gal(1→3)GalNAC(1→4)Gal(1→4)Glc(1→1)Ceramide

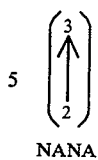

NANA

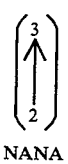

NANA

NANA where Glc stands for glucose, GalNAC stands for N-acetyl-galactosamine, Gal stands for galactose, NANA stands for N-acetylneuraminic acid.

To better illustrate the structure of the gangliosides, which is substantially the same as for the derivatives of the present invention, and in particular the character of the bonds between the saccharide moieties, the sialic acids and the ceramides, the following formula constitutes the complete formula of a "pure" ganglioside $GM_1$ containing only one sialic acid (represented by N-acetylneuraminic or N-glycolylneuraminic acid, i.e. Y=H or OH, respectively).

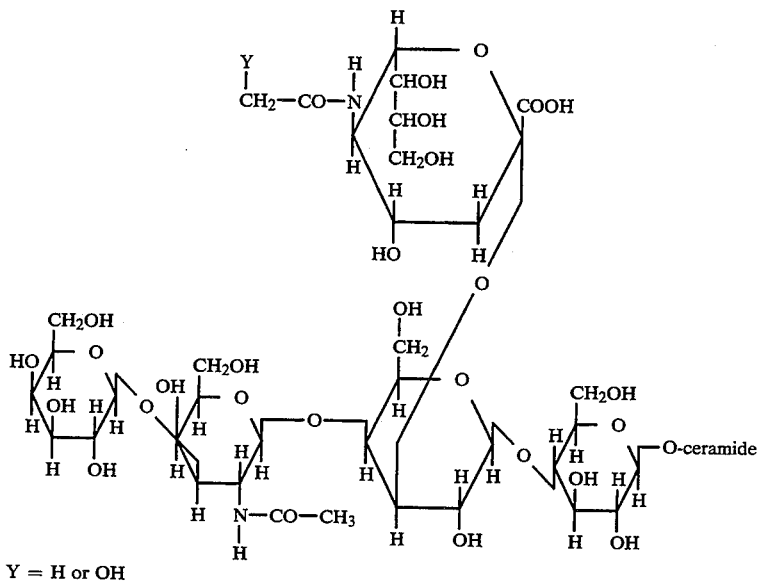

Y = H or OH

NANA

NANA $GT_{1b}$
Gal(1→3)GalNAC(1→4)Gal(1→4)Glc(1→1)Ceramide

Within the scope of the present invention are mixtures of the new ganglioside amides and in particular those deriving from the ganglioside mixtures such as are present in extracts from various animal tissues, such as in "total" extracts, or in various fractions, for example those described in the literature, for example in the above reported articles and also in the articles "Extraction and analysis of materials containing lipid bound sialic acid" in the aforesaid journal, pages 159–186 (1976) and in "Gangliosides of the Nervous System" same publication, pages 187–214, and in German patent No. 25 49 680. Among the most important ganglioside mixtures to be used as starting products are ganglioside extracts obtained from the nervous system, in particular from the brain and containing the gangliosides $GM_1$, $GD_{1a}$, $GD_{1b}$ and $GT_{1b}$ already mentioned. The basic natural gangliosides used in the preparation of the gan- N,N'-di-isovaleryl-N,N'-di-lyso $GM_1$
N,N'-di-enanthyl-N,N'-di-lyso $GM_1$
N,N'-di-pelargonoyl-N,N'-di-lyso $GM_1$
N,N'-di-tert-butylacetyl-N,N'-di-lyso $GM_1$
N,N'-di-palmitoyl-N,N'-di-lyso $GM_1$
N,N'-di-lauroyl-N,N'-di-lyso $GM_1$
N,N'-di-stearoyl-N,N'-di-lyso $GM_1$
N,N'-di-oleyl-N,N'-di-lyso $GM_1$
N,N'-di-dichloroacetyl-N,N'-di-lyso $GM_1$
N,N'-di-monochloroacetyl-N,N'-di-lyso $GM_1$
N,N'-di-(3-chloropivaloyl)-N,N'-di-lyso $GM_1$
N,N'-di-monohydroxyacetyl-N,N'-di-lyso $GM_1$
N,N'-di-trifluoroacetyl-N,N'-di-lyso $GM_1$
N,N'-di-trichloroacetyl-N,N'-di-lyso $GM_1$
N,N'-di-tribromoacetyl-N,N'-di-lyso $GM_1$
N,N'-di-monomercaptoacetyl-N,N'-di-lyso $GM_1$
N,N'-di-maleyl-N,N'-di-lyso $GM_1$
N,N'-di-(12-hydroxystearoyl)-N,N'-di-lyso $GM_1$
N,N'-di-(2-hydroxybutyryl)-N,N'-di-lyso $GM_1$
N,N'-di-monofluoroacetyl-N,N'-di-lyso $GM_1$
N,N'-di-difluoroacetyl-N,N'-di-lyso $GM_1$
N,N'-di-(3-aminopropionyl)-N,N'-di-lyso $GM_1$
N,N'-di-cyanoacetyl-N,N'-di-lyso $GM_1$
N,N'-di-(3-diethylaminopropionyl)-N,N'-di-lyso $GM_1$
N,N'-di-aminoacetyl-N,N'-di-lyso $GM_1$
N-dichloroacetyl-N'-acetyl-N,N'-di-lyso $GM_1$
N-dichloroacetyl-N'-propionyl-N,N'-di-lyso $GM_1$
N-monochloroacetyl-N'-pivaloyl-N,N'-di-lyso $GM_1$
N-monohydroxyacetyl-N'-acetyl-N,N'-di-lyso $GM_1$
N-cyanoacetyl-N'-butyryl-N,N'-di-lyso $GM_1$
N-monofluoroacetyl-N'-palmitoyl-N,N'-di-lyso $GM_1$
N-mercaptoacetyl-N'-pivaloyl-N,N'-di-lyso $GM_1$
N-trichloroacetyl-N'-formyl-N,N'-di-lyso $GM_1$
N-3-chloropivaloyl-N'-2-propylpentanoyl-N,N'-di-lyso $GM_1$
N-3-aminopropionyl-N'-oleyl-N,N'-di-lyso $GM_1$
N-aminoacetyl-N'-tert-butylacetyl-N,N'-di-lyso $GM_1$
and the corresponding derivatives of $GM_2$, $GM_3$, $GD_{1a}$, $GD_{1b}$, $GD_2$, $GT_1$, and $GT_{1b}$.

The novel ganglioside derivatives according to the present invention contain one or more amide groups, according to the number of sialic residues present in the ganglioside or basic semisynthetic derivative. In the derivatives of compounds with sialic acid residues it is also possible to prepare partial amides, i.e. compounds in which not all of the sialic acid residues are amidated, which partially amidated compounds also form part of the invention.

In the context of the present invention, an aliphatic amino acid means a compound wherein both the acid group and the amino group are bound to an aliphatic hydrocarbyl group. The amino group can be present in any position of the aliphatic chain with respect to the acid group and that is in position $\alpha$, $\beta$, $\gamma$, $\delta$, $\epsilon$ to $\omega$, and can be primary, as in glycine, or secondary as in proline. The carboxylic amino acids have preferably a maximum of 22 carbon atoms and can be substituted by other functions, such as in particular by one or more hydroxyl, amino, mercapto, alkoxy, or alkyl mercapto groups, or by one or more halogen atoms. The number of substituting functions is preferably 1–3, 1 being especially preferred. The substituting functions are preferably identical when there is more than one. Moreover, they can be substituted or interrupted in the aliphatic chain by other hydrocarbyl moieties, such as aryl, cycloalkyl, or heterocyclic moieties.

It is preferable to use naturally occurring amino acids in L-form. Specific examples of amino acids are $\alpha$-amino acids such as glycine, alanine, serine, cysteine, cystine, valine, nor-valine, leucine, isoleucine, phenylalanine, tyrosine, diiodothyrosine, tryptophan, histidine, $\alpha$-aminobutyric acid, methionine, nor-leucine, arginine, ornithine, lysine, aspartic acid, asparagine, glutamic acid, oxyglutamic acid, glutamine, dioxyphenylalanine and threonine, and $\gamma$-aminobutyric acid.

The carboxylamides of the present invention may also be derived from sulfonic amino acids, that is with a sulfonic group instead of a carboxylic acid group. These amino acids are known or can be prepared in a known way. Preference is given to sulfonic amino acids similar to the carboxylic amino acids mentioned previously, for example the natural variety of the L series. Particular examples are taurine, cysteic acid and homocysteic acid.

Preferred compounds of the invention are: the amides of gangliosides prepared with said natural amino acids, such as especially glycine, alanine, serine, valine, leucine, $\alpha$-amino and $\gamma$-amino butyric acids, glutamic acid, aspartic acid, the gangliosides being of said group (B), especially of the ganglioside $GM_1$, and of their semisynthetic derivatives such as N-acyl-N-lyso-ganglioside, N'-acyl-N'-lyso-ganglioside and N,N'-diacyl-N,N'-di-lyso-ganglioside, wherein the acyl groups are moieties from acids chosen from the group formed by lower or higher aliphatic acids, unsubstituted, with between 2 and 22 carbon atoms, especially with 2–8 and 9–22 carbon atoms, or corresponding acids with a double bond, or by aliphatic acids with between 2 and 10 carbon atoms, unsubstituted or substituted by one or two substituents of chlorine, bromine or fluorine atoms, lower hydroxy or alkoxy groups or free amino groups or mono- or dialkylated with lower hydrocarbons with a maximum of 4 carbon atoms. Preferred amides of gangliosides are the amides prepared with the starting N-acyl-N-lysogangliosides, N'-acyl-N'-lyso-gangliosides and N,N'-diacyl-N,N'-di-lyso-gangliosides as described above, especially N-acyl-N-lysogangliosides, N'-acyl-N'-lysogangliosides and N,N'-di-acyl-N,N'-di-lyso-gangliosides in which the acyl group in the first two mentioned starting materials and at least one of the acyl groups in the N,N-diacyl-N,N-di-lyso ganglioside is derived from palmitic acid, stearic acid, lauric acid, myristic acid or from a corresponding unsaturated acid, in which each compound is converted, wholly or partially, into an amide, the amino group originating from an amino acid selected from the group consisting of glycine, alanine, serine, cysteine, cystine, valine, nor-valine, leucine, isoleucine, phenylalanine, tyrosine, diiodothyrosine, tryptophan, histidine, $\alpha$-aminobutyric acid, methionine, nor-leucine, arginine, ornithine, lysine, aspartic acid, asparagine, glutamic acid, oxyglutamic acid, glutamine, dioxyphenylalanine, threonine, $\gamma$-aminobutyric acid, taurine, cysteic acid and homosysteic acid.

As stated above, the amides of the present invention have, apart from the anti-neuronotoxic properties characteristic of gangliosides, a more marked pro-neuronotrophic effect than is usually found in gangliosides. This double action can be used in therapy or in preventive measures in the above-mentioned pathologies connected with neuronal death and/or acute or chronic glioside-carboxylamide are preferably used in purified form.

Semisynthetic gangliosides of group 2 are described in the literature, for example in the following European patent applications: "New Lysoganglioside Derivatives", publication number 0373039, "Semisynthetic Analogues of Gangliosides", publication number 0410881 and "New Di-lysoganglioside Derivatives" publication number 0410883. Their amides, also generically included in said patents, have pharmacological properties similar to those of gangliosides and their amides and esters.

The present invention relates, however, to a particular selection of amides derived from aliphatic amino acids with a carboxylic or sulfonic acid function, of said semisynthetic ganglioside analogues.

As stated above, the basic semisynthetic ganglioside is selected from the group consisting of N-acyl-N-lyso-gangliosides, N'-acyl-N'-lyso-gangliosides and N,N'-diacyl-N,N'- di-lyso-gangliosides in which the N- and N'-acyl groups are identical or different and each is a moiety of an optionally substituted aliphatic acid. The optionally substituted aliphatic acid has preferably 1–24 carbon atoms and can be saturated or unsaturated.

The N-acyl-N-lyso-gangliosides used as starting compounds are obtained by first deacylating natural or purified gangliosides (of group 1) at the sphingosine nitrogen atom and then reacylating the compounds formed with a reactive derivative of an aliphatic acid, preferably an acid with between 1 and 24 carbon atoms. Of particular interest are the compounds derived from higher aliphatic acids with between 12 and 22 carbon atoms, such as palmitic, stearic, lauric or myristic acid or corresponding unsaturated acids, such as oleic or arachidonic acid.

Another particularly interesting group of acids is constituted by the aliphatic acids with between 2 and 10 carbon atoms, such as acetic acid, propionic acid, butyric acid, valerianic acid, trimethylacetic acid, enantic or capronic acid.

All these acids can also be substituted, preferably by polar units, for example by halogen atoms, such as chlorine, bromine or fluorine atoms, or by hydroxyl groups, which may be free, esterified or etherified, or by amino groups, which may be free or mono- or dialkylated. The number of polar substituents, if present, on each acyl group is 1–3, 2 being preferred. When there is more than one polar substituent present, they can be identical or different. They are preferably identical.

It is also possible to use, as starting substances for the preparation of the amides according to the present invention, N'-acyl-N'-lyso-gangliosides and N,N'-diacyl-N,N'-di-lyso-gangliosides. The N-acyl-N-lyso-gangliosides, N'-acyl-N'-lyso-gangliosides and N,N'-diacyl-N,N'-di-lyso-gangliosides can be prepared as described in e.g. the above-mentioned European patent applications. It is preferable to use the ganglioside derivatives with the acyl groups derived from acids as specified above, and the preferences mentioned above with regard to the acyl groups are also valid in the last-mentioned cases.

Interesting starting materials are

N-lauroyl-N-lyso $GM_1$
N-stearoyl-N-lyso $GM_1$
N-oleyl-N-lyso $GM_1$
N-palmitoyl-N-lyso $GM_1$
N-acetyl-N-lyso $GM_1$
N-propionyl-N-lyso $GM_1$
N-butyryl-N-lyso $GM_1$
N-valeroyl-N-lyso $GM_1$
N-trimethylacetyl-N-lyso $GM_1$
N-enantoyl-N-lyso $GM_1$
N-caproyl-N-lyso $GM_1$
N-dichloracetyl-N-lyso $GM_1$
N-chloracetyl-N-lyso $GM_1$
N-3-chloropivaloyl-N-lyso $GM_1$
N-hydroxyacetyl-N-lyso $GM_1$
N-trifluoroacetyl-N-lyso $GM_1$
N-tribromoacetyl-N-lyso $GM_1$
N-mercaptoacetyl-N-lyso $GM_1$
N-maleyl-N-lyso $GM_1$
N-12-hydroxystearoyl-N-lyso $GM_1$
N-2-hydroxybutyroyl-N-lyso $GM_1$
N-fluoroacetyl-N-lyso $GM_1$
N-difluoroacetyl-N-lyso $GM_1$
N-3-aminopropionyl-N-lyso $GM_1$
N-cyanoacetyl-N-lyso $GM_1$
N-(3-diethylaminopropionyl)-N-lyso $GM_1$
N-aminoacetyl-N-lyso $GM_1$
N'-lauroyl-N'-lyso $GM_1$
N'-stearoyl-N'-lyso $GM_1$
N'-oleyl-N'-lyso $GM_1$
N'-palmitoyl-N'-lyso $GM_1$
N'-acetyl-N'-lyso $GM_1$
N'-propionyl-N'-lyso $GM_1$
N'-butyryl-N'-lyso $GM_1$
N'-valeroyl-N'-lyso $GM_1$
N'-trimethylacetyl-N'-lyso $GM_1$
N'-enantoyl-N'-lyso $GM_1$
N'-caproyl-N'-lyso $GM_1$
N'-dichloracetyl-N'-lyso $GM_1$
N'-chloracetyl-N'-lyso $GM_1$
N'-3-chloropivaloyl-N'-lyso $GM_1$
N'-hydroxyacetyl-N'-lyso $GM_1$
N'-trifluoroacetyl-N'-lyso $GM_1$
N'-tribromoacetyl-N'-lyso $GM_1$
N'-mercaptoacetyl-N'-lyso $GM_1$
N'-maleyl-N'-lyso $GM_1$
N'-12-hydroxystearoyl-N'-lyso $GM_1$
N'-2-hydroxybutyroyl-N'-lyso $GM_1$
N'-fluoroacetyl-N'-lyso $GM_1$
N'-difluoroacetyl-N'-lyso $GM_1$
N'-3-aminopropionyl-N'-lyso $GM_1$
N'-cyanoacetyl-N'-lyso $GM_1$
N'-(3-diethylaminopropionyl)-N'-lyso $GM_1$
N'-aminoacetyl-N'-lyso $GM_1$
N,N'-di-formyl-N,N'-di-lyso $GM_1$
N,N'-di-acetyl-N,N'-di-lyso $GM_1$
N,N-di-propionyl-N,N'-di-lyso $GM_1$
N,N-di-butyryl-N,N'-di-lyso $GM_1$
N,N'-di-pivaloyl-N,N'-di-lyso $GM_1$
N,N'-di-valeryl-N,N'-di-lyso $GM_1$
N,N'-di-octanoyl-N,N'-di-lyso $GM_1$
N,N'-di-lauroyl-N,N'-di-lyso $GM_1$
N,N'-di-2-propylpentanoyl-N,N'-di-lyso $GM_1$
N,N'-di-hexanoyl-N,N'-di-lyso $GM_1$ neuronal deficit where it is necessary to limit neurodegenerative phenomena while promoting to the utmost neuronal plasticity to facilitate the recovery of impaired neurological functions.

Experimental and clinical research has amply demonstrated the prominent role of excitatory amino acids (EAA) such as glutamate and aspartate in excitatory neurotransmission of the vertebrate CNS. It has been suggested that EAA are involved in development, in a variety of physiological processes such as neuronal survival, reinforcement of the axonal structure, synaptogenesis and synaptic plasticity deriving from nervous activity. EAA also play a fundamental role in modelling neuronal circuits and in learning and memory phenomena.

It has been demonstrated that the physiological activity of glutamate receptors induces a sequences of events, including the activation of "early genes" (such as proto-oncogenes C-fos and C-Jun) which precedes, in turn, a series of neuroplastic events. Indeed, the transduction mechanisms physiologically activated by glutamate induce an increase in C-fos-mRNA and hence nuclear accumulation of the relative coded protein, which in turn promotes the coordinated expression of specific mRNA encoding proteins which mediate long-term responses of physiological stimulation of the glutamate receptor, such as neuronal plasticity.

There are reports of increasing evidence that in conditions of cerebral suffering there is continuous, paroxysmal release of glutamate:

at the basis of secondary cerebral damage, in the area around an anoxic, traumatic or hypoglycemic lesion, there is therefore an uncontrolled release of glutamate and consequent protracted "abusive" activation of the excitatory amino acid receptors.

This results in continuous activation of the calcium channel with consequent increase in cytoplasmic $Ca^{++}$ and hence permanent protein kinase C (PKC) activation: a cascade of events is triggered of which leads to the activation of cell processes resulting inevitably in neuronal death.

In view of these facts it is clearly important to research new pharmacological agents able to physiologically modulate neuronoplastic ("pro-neuronotrophic activity") and neuronotoxic mechanisms ("antineuronotoxic activity"). Regarding the neuronotoxic aspect, increasing validity has been acquired in recent years by a new pharmacological approach, differing from other "aspecific" therapies (e.g. glutamate receptor isoteric antagonists) which indiscriminately block all the glutamate receptors present in the brain, causing severe side effects.

In contrast hereto, this new pharmacological approach involves the use of drugs acting solely where there is an ongoing neurotoxic mechanism. This class of drugs, which has been given the name "RADA" (Receptor Abuse-Dependent Antagonists) antagonizes the pathological effects of paroxystic and continuous (abusive) stimulation of excitatory amino acid receptors. Gangliosides belong to this category of drugs, known as RADA.

In particular, regarding the aforesaid protective effect against glutamate-induced neurotoxicity, it has been reported that pretreatment with natural glycosphingolipids (Favaron M. et al.: Gangliosides prevent glutamate and kainate neurotoxicity in primary neuronal cultures of neonatal rat cerebellum and cortex. Proc. Natl. Acad. Sci. 85: 7351-7355, 1988) reduces neuronal death, deriving from prolonged abusive activation of EAA receptors, both in normal and anoxic conditions (Facci L. et al.: Monosialoganglioside protects against anoxic and kainic-acid-induced neuronal death in vitro, J. Neuroch. vol. 52, (Suppl.) S: 183, 1989). It has also been reported that structural changes in ganglioside molecules, such as in the number of sialic residues and/or substitution in the basic sphingolipid structure, decide the strength and efficacy of said sphingolipids in preventing neuronal death induced by glutamate and in inhibiting PKC (Costa E. et al.: Signal transduction at excitatory amino acid receptors: modulation by gangliosides. Neurology and neurobiology 46: 29-38 1988). It should be noted that these effects of gangliosides do not inhibit receptor function, but they are brought about by antagonism of the consequences of abusive stimulation of glutamate receptors (i.e. prolonged high levels of cytosolic $Ca^{++}$ and persistent PKC activation). It is therefore a RADA effect, since the block of glutamate neurotoxicity comes about downstream from the receptor, preventing the effects of its "paroxysmal activation" without modifying the physiology of syntaptic transmission by glutamate.

In the studies carried out to date no association has been observed between the antineuronotoxic effect of gangliosides and variations in C-fos, the gene whose activation (as cited above) precedes a series of neuronoplastic events.

Apart from the antineuronotoxic properties characteristic of gangliosides, the amides of the present invention have a marked proneuronotrophic effect which is greater than that of gangliosides. The abovesaid effects of the new products of the present invention can be demonstrated by the following experiments carried out on a typical product according to the present invention, the glycinamide of the ganglioside $GM_1$, which will hereafter be known as $AGF_{118}$. In particular, the following experiments were effected in vitro:

1. proneuronotrophic effect in cerebellar granule cell cultures: content of C-fos mRNA and C-Jun mRNA following glutamate-induced stimulation
2. protective effect on endogenous-glutamate-induced neurotoxicity The effects thus measured are comparable to corresponding effects obtained with ganglioside $GM_1$ or with $GM_1$ and its esters or amides respectively.

1. Proneuronotrophic effect of $AGF_{118}$ (vs $GM_1$) in cerebellar granule cell cultures: content of C-fos mRNA and C-Jun mRNA after glutamate-induced stimulation

OBJECTIVE

The present experiments were aimed at assessing the proneuronotrophic activity of the glycinamide derivative of $GM_1$ in comparison with the $GM_1$ progenitor in a model of physiological activation of the glutamate receptor. The proneuronotrophic activity was assessed in terms of increase in proto-oncogenes C-fos and C-Jun (assessed as content of the relative mRNA). It is indeed reported in the literature that the physiological activation of the glutamate receptors induces a sequence of events including activation of the C-fos proto-oncogene which in turn precedes a series of neuroplastic events (with synthesis of specific proteins with neuronotrophic activity).It has also been reported that the antineuronotoxic activity of gangliosides ($GT_{1b}$) is not associated with variations in C-fos (Favaron M. et al.: Gangliosides prevent glutamate and kainate neurotoxicity in primary neuronal cultures of neonatal rat cerebellum and cortex. Proc. Natl. Acad. Sci. 85: 7351–7355, 1988) in conditions of prolonged stimulation of the glutamate receptor.

MATERIALS AND METHODS

Cell Cultures

Primary cultures of cerebellar granule cells were prepared from 8-day-old Sprague-Dawley rats (Gallo V. et al.: Selective release of glutamate from cerebellar granule cells differentiating in culture. Proc. Natl. Acad. Sci. USA 79, 7919–7923, 1982).

The cultures were grown for 7–8 days in 35 mm dishes in the presence of specific culture medium and in humidified conditions (95% air and 5% $CO_2$) at 37° C. At said times the cells were mainly constituted by granule cells (<95%) with a small percentage (<5%) of gial cells (Alho H. et al.: Subset of GABAergic neurons in dissociated cell cultures of neonatal rat cerebral cortex show colocalization with specific modulator peptides. Dev. Brain res. 39: 193–204, 1988). Glial proliferation was prevented with cytosine arabinofuranoside.

Test products (Solubilization and concentrations)
The following products were tested:
monosialoganglioside $GM_1$ ($GM_1$)
glycinamide of $GM_1$ ($AGF_{118}$)
The gangliosides ($10^{-4}M$) were diluted in methanol/-$H_2O$(95:5) under nitrogen current, and a suitable volume of Locke's solution was added to reach the final concentration.

Exposure to Glutamate (+PCP) and Test Products ($AGF_{118}$-$GM_1$)

The cell cultures (at days 7–8) were incubated (2 hr at 37° C.) in the presence of the test products ($AGF_{118}$-$GM_1$).

The cultures were then washed 3 times with Locke's solution (1 ml) and in the absence of magnesium and then incubated with glutamate (10 $\mu$M) for 30 minutes. After incubation with glutamate±phencyclidine (PCP 1 $\mu$M), the cell monolayers were washed (3 times) with Locke's solution, specific conditioned culture medium was added, and they were incubated for 24 hrs in humidified conditions (as described above).

RNA Extraction and Northern Blot

The techniques described by Szekely et al. were used (Szekely A. M. et al.: Activation of specific glutamate receptor subtypes increases C-fos proto-oncogene expression in primary cultures of neonatal rat cerebellar granule cells. Neuropharmacology, vol. 26: n 12: 1779–1782, 1987). In short, the cells ($2 \times 10^8$/specimen) were gathered and the total RNA was isolated using cesium chloride/isothiocyanato guanidine in ultracentrifuge gradient.

Poly($A^+$) RNA was selected on oligo (dT) cellulose chromatography and fractioned on 1.1% agarose in 2.2M formaldehyde, then transferred onto nitrocellulose (in $20 \times SSC$). After heating to 80° C. for 2 hrs the filters were prehybridized to 42° C. for 2–5 hrs. The Sau I 1.2 kb fragment was used, which codes for hexone 4 of the C-fos gene from mouse derived from a C-fos clone as previously described (Curran R. et al.: Structure of the FBJ murine osteosarcoma virus genome: molecular cloning of its associated helper virus and the cellular homolog of the v-fos gene from mouse and human cells. Mol. Cell. Biol. 3: 914–921, 1983). The specific activity of the translated probe fraction (labelled with $^{32}P$) was from $5 \times 10^8$ to $10^9$ cpm/$\mu$g. The quantity of C-fos mRNA in the various samples was measured by laser densitometry LKB 2002 ultrascan and corrected for variations in the amount of poly($A^+$) RNA applied onto the gel using as a reference standard the hybridization on the cDNA probe for the structural beta-actin protein. Hybridization was effected at 42° C. for 16–20 hrs in specific conditions and then the probe filters for the C-fos and beta-actina were washed and exposed to Kodak x-Omat film at an intensity which discriminates at −70° C.

The C-fos mRNA content, revealed in the blots, was expressed in arbitrary units, wherein 1 unit is defined as the area of the densitometric peak of hybridization of the C-fos mRNA divided by the corresponding area of the densitometric peak of the hybridization of the beta-actinmRNA (used as reference standard).

A similar procedure was followed to determine the mRNA content relative to C-Jun.

RESULTS

The results obtained show a marked effect of $AGF_{118}$ on the content of both C-fos mRNA and C-Jun mRNA (in contrast to the mild stimulation induced by $GM_1$). In particular, the data relative to the mRNA content of C-fos (Tab. 1) and C-Jun (Tab. 2) indicate that:
- glutamate induces an increase in mRNA content in both genes
- preincubation with $GM_1$ ($10^{-4}M \times 2$ hr) does not substantially influence the effect of glutamate (the content of C-fos and C-Jun mRNA is only slightly higher in the presence of $GM_1$)
- preincubation with $AGF_{118}$ ($10^{-4}M \times 2$ hr) notably potentiates the increase in C-fos and C-Jun mRNA, stimulated by glutamate.

This finding therefore indicates an interesting proneuronotrophic effect of $AGF_{118}$, notably greater than that of $GM_1$.

TABLE 1

Effect of $AGF_{118}$ and $GM_1$ on the content of C-fos/mRNA induced by the physiological stimulation of the glutamate receptor in cerebellar cultures

| Samples* | mRNA content (arbitrary units)** |
|---|---|
| Control | 1 |
| Glutamate | 8.9 |
| Glutamate + $GM_1$ | 10 |
| Glutamate + $AGF_{118}$ | 20 |

*The test products were tested at $10^{-4}M$ (preincubation for 2 hr)
**Assessment after stimulation with glutamate (10 $\mu$M × 30 min) + PCP (1 $\mu$M × 30 min). Data are the means of 4 replications per sample.

TABLE 2

Effect of $AGF_{118}$ and $GM_1$ on the content of C-Jun/mRNA induced by the physiological stimulation of the glutamate receptor in cerebellar cultures

| Samples* | mRNA content (arbitrary units)** |
|---|---|
| Control | 1 |
| Glutamate | 3.8 |
| Glutamate + $GM_1$ | 5 |
| Glutamate + $AGF_{118}$ | 8.8 |

*The test products were tested at $10^{-4}M$ (preincubation for 2 hrs)
**Assessment after stimulation with glutamate (10 $\mu$M × 30 min) + PCP (1 $\mu$M × 30 min). Data are the means of 4 replications per sample.

2. Protective effect of $AGF_{118}$ (vs $GM_1$, amides and esters of $GM_1$) on neurotoxicity induced by endogenous glutamate

OBJECTIVE

The present experiments were aimed at assessing the protective activity of the glycinamide derivative of $GM_1$ on neurotoxicity induced by endogenous glutamate.

A comparative study was effected with the progenitor ganglioside $GM_1$ and other amide and ester derivatives of $GM_1$ (known products already described in the U.S. Pat. No. 4,713,374 issued on Dec. 15, 1987) in a model of hypoglycemic neurotoxicity (Facci L. et al.: Hypoglycemic neurotoxicity in vitro: involvement of excitatory amino acid receptors and attenuation by monosialoganglioside $GM_1$. In press Neuroscience, 1990).

MATERIALS AND METHODS

Cell Cultures

Cerebellar granule cell cultures were used, prepared from 8-day-old Sprague Dawley rats (Gallo V. et al.: Selective release of glutamate from cerebellar granule cells differentiating in culture. Proc. Natl. Acad. Sci. USA 79, 7919-7923, 1982) with the previously described characteristics.

The cultures ($3 \times 10^6$ cells/dish) were used on the 11th day.

Test Products and Relative Solubilization

The following products were tested:
monosialoganglioside $GM_1$ ($GM_1$)
glycinamide of $GM_1$ ($AGF_{118}$)
methylamide of $GM_1$ ($AGF_{12}$)
diethylamide of $GM_1$ ($AGF_{22}$)
benzylamide of $GM_1$ ($AGF_{16}$)
isopropylamide of $GM_1$ ($AGF_{18}$)
N-pyrrolidine 2-ethylamide of $GM_1$ ($AGF_{108}$)
ethyl ester of $GM_1$ ($AGF_{42}$)
benzyl ester of $GM_1$ ($AGF_{48}$)

The $GM_1$ and the relative ganglioside derivatives were solubilized in chloroform/metanolo (2:1), dried under nitrogen current and resuspended in Locke's solution (in the presence of $Mg^{2+}$) and in the absence of glucose.

The concentration for the various products was $5 \times 10^{-5}M$.

Induction of Neurotoxicity by Glucose Deprivation

The culture medium was syphoned from the dishes (suitably stored) and substituted with glucose-free Locke's solution (in the presence of $Mg^{2+}$). This solution was used for 3 washes and then the solutions containing the test products were added ($5 \times 10^{-5}M$) and incubated for 4 hrs in an incubator at 37° C. (5% $CO_2$). (Likewise the control cultures were incubated for 4 hrs with Locke's solution containing glucose). The treated cells were then washed with Locke's solution containing $Mg^{2+}$ and glucose and incubated in the presence of the initial culture (suitably stored) for 24 hr at 37° C. in an incubator (5% $CO_2$).

At the end of incubation cell viability was assessed and quantified by the colorimetric assay MTT (Mosmann T.: Rapid colorimetric assay for cellular growth and survival: application to proliferation and cytotoxicity assays J. Immunol. Meth. 65, 55:63, 1983) and expressed also as % of survival compared to controls, not deprived of glucose.

RESULTS

The data (Tab. 3) indicate that $GM_1$ and the various derivatives tested are all able to protect granule cells from neurotoxicity induced by endogenous glutamate.

In particular, it should be noted that the effect of preincubation with $AGF_{118}$, is comparable, and even greater than that of $GM_1$.

The other ganglioside derivatives, both ester and amide, such as $GM_1$, have protective activity.

TABLE 3

Effect of $AGF_{118}$ (vs $GM_1$ and other amide and ester derivatives of $GM_1$) on neurotoxicity induced by endogenous glutamate

| Samples* | MTT values | % survival |
| --- | --- | --- |
| + glucose (control) | 0.146 | 100 |
| − glucose | 0.067 | 46 |
| − glucose + $GM_1$ | 0.143 | 98 |
| − glucose + $AGF_{118}$ | 0.168 | 115 |
| − glucose + $AGF_{12}$ | 0.147 | 101 |
| − glucose + $AGF_{22}$ | 0.131 | 90 |
| − glucose + $AGF_{16}$ | 0.094 | 64 |
| − glucose + $AGF_{18}$ | 0.129 | 88 |
| − glucose + $AGF_{108}$ | 0.109 | 75 |
| − glucose + $AGF_{42}$ | 0.099 | 68 |
| − glucose + $AGF_{48}$ | 0.102 | 70 |

*The products were tested at a concentration of $5 \times 10^{-5}M$ ($\times$ 4 hr a 37° C.). Data are means of 4 replications per sample.

The aforesaid activities render the new carboxylamides according to the present invention suitable for pharmacological application in various central nervous system pathologies wherein it is necessary to potentiate neuronotrophic effects and to protect against neurotoxicity induced by excitatory amino acids. They are particularly indicated in therapy for pathologies wherein there is neuronal damage such as hypoxia-ischemia, hypoglycemia, epilepsy, trauma, cerebral aging, chronic and toxic-infective neurodegenerative diseases.

Interesting compounds according to the present invention are:

the amide of the glycine of ganglioside $GM_1$
the amide of the L-alanine of ganglioside $GM_1$
the amide of the L-serine of ganglioside $GM_1$
the amide of the γ-aminobutyric acid of ganglioside $GM_1$
the amide of the L-cysteine of ganglioside $GM_1$
the amide of the taurine of ganglioside $GM_1$
the amide of the cysteic acid of ganglioside $GM_1$
the amide of the homocysteic acid of ganglioside $GM_1$
the amide of the glycine of N-lauroyl-N-lyso-$GM_1$
the amide of the glycine of N-stearoyl-N-lyso-$GM_1$
the amide of the L-alanine of N-oleyl-N-lyso-$GM_1$
the amide of the L-alanine of N-palmitoyl-N-lyso-$GM_1$
the amide of the L-serine of N-acetyl-N-lyso-$GM_1$
the amide of the γ-aminobutyric acid of N-propionyl-N-lyso-$GM_1$
the amide of the L-cysteine of N-valeryl-N-lyso-$GM_1$
the amide of the glycine of N'-lauroyl-N'-lyso-$GM_1$
the amide of the glycine of N'-stearoyl-N'-lyso-$GM_1$
the amide of the L-alanine of N'-oleyl-N'-lyso-$GM_1$
the amide of the L-alanine of N'-palmitoyl-N'-lyso-$GM_1$
the amide of the L-serine of N'-acetyl-N'-lyso-$GM_1$
the amide of the γ-aminobutyric acid of N'-propionyl-N'-lyso-$GM_1$ the amide of the L-cysteine of N'-valeryl-N'-lyso-GM$_1$
the amide of the glycine of N,N'-dilauroyl-N,N'-di-lyso-GM$_1$
the amide of the glycine of N,N'-distearoyl-N,N'-di-lyso-GM$_1$
the amide of the L-alanine of N,N'-dioleyl-N,N'-di-lyso-GM$_1$
the amide of the L-alanine of N,N'-dipalmitoyl-N,N'-di-lyso-GM$_1$
the amide of the L-serine of N,N'-diacetyl-N,N'-di-lyso-GM$_1$
the amide of the γ-aminobutyric acid of N,N'-dipropionyl-N,N'-di-lyso GM$_1$
the amide of the L-cysteine of N,N'-divaleryl-N,N'-di-lyso-GM$_1$
the amide of the taurine of N-acetyl-N-lyso-GM$_1$
the amide of the taurine of N'-lauryl-N'-lyso-GM$_1$
the amide of the taurine of N,N'-dioleyl-N,N'-di-lyso-GM$_1$
the amide of the cysteic acid of N-propionyl-N-lyso-GM$_1$
the amide of the cysteic acid of N'-stearoyl-N'-lyso-GM$_1$
the amide of the cysteic acid of N,N'-divaleryl-N,N'-di-lyso-GM$_1$
and the compounds corresponding to all these having as a ganglioside base, in the place of GM$_1$, a ganglioside chosen from the group formed by gangliosides GD$_{1a}$, GD$_{1b}$ and GT$_{1b}$.

The present invention also includes processes for the preparation of the new amides of gangliosides and their aforesaid semisynthetic derivatives. The processes are essentially those already described in said U.S. Pat. No. 4,713,374 and they include the following methods:

a) reaction of the inner esters of gangliosides or their semisynthetic derivatives with the amino acids, the amide groups of which are to be introduced.

b) reaction of the carboxylic esters of gangliosides or their semisynthetic derivatives with the amino acids, the amide groups of which are to be introduced.

c) reaction of gangliosides or their said semisynthetic derivatives with the amino acid corresponding to the amide group to be introduced and wherein the carboxylic or sulfonic acid function in said amino acid is protected.

Reaction a) can be performed by direct treatment, with or without a solvent, of the ganglioside (or of the analogous semisynthetic derivative) in the form of its inner ester with the amino acid. The reaction can also be performed at quite low temperatures, such as between −5° and +10° C., but preferably at room temperature or above, for example between 30° and 120° C. Ketones, aromatic hydrocarbons, dimethylformamide, dimethylsulfoxide, dioxane or tetrahydrofuran can be used as solvents. Reaction b) is also performed preferably under the conditions described for a). Apart from the aliphatic esters, other esters can also be used, for example esters with phenols.

The reaction c) in methods known in peptide chemistry are used to activate the carboxy group, avoiding those involving too acid or too basic conditions which would lead to the disintegration of the ganglioside molecule or semisynthetic analogue. If the starting gangliosides are in the form of sodium salts for example, it is advisable first to treat the salt with a Dowex-type ion exchange resin or another acid ion exchanger. For example, it is possible to use the method of condensation in the presence of carbodiimides such as dicyclohexylcarbodiimide, benzylisopropylcarbodiimide or benzylethylcarbodiimide, in the presence of 1-hydroxybenzotriazol or condensation in the presence of N,N'-carbonyldiimidazol.

Compounds obtained according to said processes can, if desired, be converted into their salts, which are also part of the invention and can themselves be used to prepare the medicaments to be used in therapy like the free compounds. Due to the essential equivalence between salts and free-form amides, that what is stated above for the free-form compounds, especially regarding pharmaceutical applications and medicaments, is also valid for the corresponding salts, as long as these are therapeutically acceptable salts, which therefore form a preferred object of the present invention. The salts can however also be used for the purification of the amides and in this case it is possible to use for said salification also bases or acids which are not therapeutically useful, for example the salts of picric or picrolinic acids.

The salts can be those wherein the carboxyls or the sulfonic groups of the amino acids present are salified with metals or organic bases. Therapeutically acceptable salts of this type are for example: alkaline metal salts, for example sodium, potassium, and lithium salts and alkaline earth metal salts, such as calcium or magnesium salts. It is also possible to use, if desired, heavy metal salts, such as iron salts. Organic base salts can then be prepared, for example of primary, secondary or tertiary, aliphatic or aromatic or heterocyclic amines such as methylamine, ethylamine, propylamine, piperidine, morpholine, ephedrine, furfurylamine, choline, ethylenediamine and aminoethanol.

A second group of salts is constituted by salts obtained by acid addition, especially in cases where a free amino function is present in the amide component. Particular mention should be made of salts with mineral acids, such as hydrochloric acid, hydrobromic acid, phosphoric acid and sulfuric acid, and with lower aliphatic acids with a maximum of 7 carbon atoms, such as formic, acetic, propionic, succinic or maleic acid.

Another object of the present invention are pharmaceutical preparations containing as active substance one or more of the novel amide derivatives defined above, and in particular, those especially mentioned, such as those of ganglioside groups A and B and those specifically listed or those described in the illustrative Examples. Such pharmaceutical preparations can be for oral, rectal, parenteral, local or intradermal use. They are therefore in solid or semisolid form, for example pills, tablets, gelatin capsules, capsules or soft gelatin suppositories. For parenteral use, the forms intended for intramuscular, subcutaneous or intradermal administration or for infusions or injection can be used, and they can therefore be prepared as solutions of the active compounds or as freeze-dried powders of the active compounds to be mixed with one or more excipients or pharmaceutically acceptable diluents which are suitable for the above uses and have an osmolarity which is compatible with the physiological fluids. The pharmaceutical preparations may comprise ordinary pharmaceutically acceptable excipients such as diluents, binders, flavorings, colorants, preservatives and disintegrants, in accordance with usual pharmaceutical practice, in a manner known to the skilled person in the formulation of preparations with gangliosides. For local use, preparations in the form of sprays, such as nose sprays, creams or ointments for topical use or suitable treated plasters for intradermal administration should be considered. The preparations of the invention can be administered to humans or animals.

The ganglioside derivatives according to the invention may be present in the pharmaceutical preparations as the only active ingredient or in combination with other pharmaceutically active ingredients.

The preparations contain preferably 0.01% to 10% of the active component for the solutions, sprays, ointments and creams and between 1% and 100% and preferably between 5% and 50% of the active compound for preparations in solid form. Doses to be administered depend on the indication, on the desired effect and on the chosen route of administration.

For the therapeutic, or possibly only preventive application by parenteral route, the doses vary preferably between 0.05 mg and 10 mg of active substance per kg of body weight/day and especially between 0.05 and 2 mg per kg of body weight/day.

Still another object of the invention relates to a method for the treatment of nervous system pathologies, both central nervous system pathologies and peripheral nervous system pathologies. An interesting aspect of the invention relates to a method for the treatment of pathologies connected to neuronal damage, especially hypoxia-ischemia, hypoglycemia, epilepsy, trauma, cerebral aging, chronic and toxic-infective neurogenerative diseases. The invention is illustrated by the following nonlimiting Examples.

EXAMPLE 1

10 g of inner ester (6.6 mmol) of $GM_1$ are dissolved in 100 ml of anhydrous pyridine. To the solution are added 3.2 g of (1)-glycine-methylester. HCl (5:1) and 5 ml of triethylamine. It is left to react at 40° C. for 24 hrs.

The solution is dried and gathered with 50 ml of $Na_2CO_3$, 0.01M. It is left to stand for 1 hr at 60° C. The solution is then dialyzed against 5 volumes of distilled water.

It is dried and chromatographed on silica gel column eluting with chloroform/methanol/$H_2O$($NH_4$)$_2CO_3$ 60/35/8, to eliminate the non-reacted $GM_1$.

Yield of dry product: g 4.5.

Silica gel chromatography, using as solvent chloroform/methanol/$CaCl_2$ 0.3% (60:35:8), shows the product to be the amide of glycine of ganglioside $GM_1$ with Rf=0.42 ($GM_1$=0.4).

EXAMPLE 2

10 g of inner ester (6.6 mmol) of $GM_1$ are dissolved in 100 ml of anhydrous pyridine. To the solution are added 4.5 g of L-alanine-methylester. HCl (5:1) and 5 ml of triethylamine. It is left to react at 40° C. for 24 hrs.

The solution is dried and gathered with 50 ml of $Na_2CO_3$ 0.01M. It is left to stand for 1 hr at 60° C. The solution is then dialyzed against 5 volumes of distilled water.

It is dried and chromatographed on silica gel column eluting with chloroform/methanol/$H_2O$ ($NH_4$)$_2CO_3$ 60/35/8, to eliminate the non-reacted $GM_1$.

Yield in dry product: g 4.3.

Silica gel chromatography, using as solvent chloroform/methanol/$CaCl_2$ 0.3% (60:35:8), shows the product to be the amide of L-alanine of the ganglioside $GM_1$ with Rf=0.61 ($GM_1$=0.4).

EXAMPLE 3

10 g of inner ester (6.6 mmol) of $GM_1$ are dissolved in 100 ml of anhydrous pyridine. To the solution are added 5 g of L-serine-methylester.HCl (5:1) and 5 ml of triethylamine. It is left to react at 40° C. for 24 hrs.

The solution is dried and gathered with 50 ml of $Na_2CO_3$ 0.01M. It is left to stand for 1 hr at 60° C. The solution is then dialyzed against 5 volumes of distilled water.

It is dried and chromatographed on silica gel column eluting with chloroform/methanol/$H_2O$ ($NH_4$)$_2CO_3$ 60/35/8, to eliminate the non-reacted $GM_1$.

Yield in dry product: g 4.

Silica gel chromatography, using as solvent chloroform/methanol/$CaCl_2$ 0.3% (60:35:8), shows the product to be the amide of L-serine of ganglioside $GM_1$ with Rf=0.58 ($GM_1$=0.4).

EXAMPLE 4

10 g of inner ester (6.6 mmol) of $GM_1$ are dissolved in 100 ml of anhydrous pyridine. To the solution are added 5 g of γ-aminobutyric-methylester.HCl (5:1) and 5 ml of triethylamine. It is left to react at 40° C. for 24 hrs.

The solution is dried and gathered with 50 ml of $Na_2CO_3$ 0.01M. It is left to stand for 1 hr at 60° C. The solution is then dialyzed against 5 volumes of distilled water.

It is dried and chromatographed on silica gel column eluting with chloroform/methanol/$H_2O$ ($NH_4$)$_2CO_3$ 60/35/8, to eliminate the non-reacted $GM_1$.

Yield in dry product: g 3.

Silica gel chromatography, using as solvent chloroform/methanol/$CaCl_2$ 0.3% (60:35:8), shows the product to be the amide of γ-aminobutyric acid of ganglioside $GM_1$ with Rf=0.27 ($GM_1$=0.4).

EXAMPLE 5

10 g of inner ester (6.6 mmol) of $GM_1$ are dissolved in 100 ml of anhydrous pyridine. To the solution are added 3.9 g of L-cysteine (5:1) and 5 ml of triethylamine. It is left to react at 40° C. for 24 hrs.

The solution is filtered to eliminate the non-reacted cysteine and then dried.

It is chromatographed on silica gel column eluting with chloroform/methanol/$H_2O$ ($NH_4$)$_2CO_3$ 60/35/8, to eliminate the non-reacted $GM_1$.

Yield in dry product: g 4.5.

Silica gel chromatography, using as solvent chloroform/methanol/$CaCl_2$ 0.3% (60:35:8), shows the product to be the amide of L-cysteine of ganglioside $GM_1$ with Rf=0.31 ($GM_1$=0.4).

EXAMPLE 6

In 10 ml of water/tetrahydrofuran 1:3, kept at pH 4.7 with HCl 0.1N in pH-controlled conditions, the following are dissolved in this order: 500 mg (3.9 mmol) of 2-aminoethanesulfonic acid (taurine), 500 mg (0.22 mmol) of peracylated $GM_1$ and 1.25 g (6.5 mmol) of 1-(3-dimethylaminopropyl)-3-ethylcarbodiimide. The reaction is performed at room temperature for 4 hrs. Lastly, the raw product is vacuum-dried, treated with 10 ml of $Na_2CO_3$ 1N at 70° C. for 24 hrs, dialyzed against distilled water and vacuum-dried again. The final purification is performed by silica gel chromatography, eluting with a mixture of chloroform/methanol/water 60:35:8.

Yield in dry product: 85 mg (23% theoretical).

Silica gel chromatography, using as solvent chloroform/methanol/CaCl$_2$ 0.3% (50:42:11), shows the product to be the amide of taurine of ganglioside GM$_1$, with Rf=0.53 (GM$_1$=0.43).

EXAMPLE 7

Pharmaceutical Preparations in Solution for Injection

| Preparation No. 1 - one 2-ml ampule contains: | | |
|---|---|---|
| active substance | mg | 5 |
| sodium chloride | mg | 16 |
| citrate buffer pH 6 in water | ml | 2 |
| for injection q.s. ad | | |
| Preparation No. 2 - one 2-ml ampule contains: | | |
| active substance | mg | 50 |
| sodium chloride | mg | 16 |
| citrate buffer pH 6 in water | ml | 2 |
| for injection q.s. ad | | |
| Preparation No. 3 - one 4-ml vial contains: | | |
| active substance | mg | 100 |
| sodium chloride | mg | 32 |
| citrate buffer pH 6 in water | ml | 4 |
| for injection q.s. ad | | |

EXAMPLE 8

Pharmaceutical Compositions Prepared in Twin Vials

The preparations illustrated in these Examples are prepared in twin vials. The first vial contains the active substance in the form of a freeze-dried powder in quantities which may vary between 10% and 90% in weight, together with a pharmaceutically acceptable excipient, with glycine or mannitol. The second vial contains the solvent, as a sodium chloride solution and a citrate buffer.

| System No. 1 | | |
|---|---|---|
| a. one 2-ml freeze-dried vial contains: | | |
| active substance | mg | 5 |
| glycine | mg | 30 |
| b. one 2-ml ampule of solvent contains: | | |
| sodium chloride | mg | 16 |
| citrate buffer in | ml | 2 |
| water for injection q.s. ad | | |
| System No. 2 | | |
| a. one 3-ml freeze-dried vial contains: | | |
| active substance | mg | 50 |
| glycine | mg | 25 |
| b. one 3-ml ampule of solvent contains: | | |
| sodium chloride | mg | 24 |
| citrate buffer in | ml | 3 |
| water for injection q.s. ad | | |
| System No. 3 | | |
| a. one 5-ml freeze-dried vial contains: | | |
| active substance | mg | 150 |
| glycine | mg | 50 |
| b. one 4-ml ampule of solvent contains: | | |
| sodium chloride | mg | 32 |
| citrate buffer in | ml | 4 |
| water for injection q.s. ad | | |

The following is claimed:

1. A ganglioside derivative comprised of a basic natural or semisynthetic ganglioside, the carboxyl group in the sialic part of said natural or semisynthetic ganglioside being converted into a carboxylamide with an aliphatic amino acid or amino sulfonic acid, or a salt thereof with metals or organic bases on free carboxy or sulfonic groups or acid addition salts on any free amino groups.

2. The ganglioside according to claim 1 in which the semisynthetic ganglioside is selected from the group consisting of N-acyl-N-lyso-gangliosides, N'-acyl-N'-lyso-gangliosides and N,N'-diacyl-N,N'-di-lyso-gangliosides in which the N- and N'-acyl groups are the same or different and each is a moiety of an optionally substituted aliphatic acid.

3. The ganglioside derivative according to claim 1, wherein the basic natural ganglioside is obtained from tissues and organs of the nervous system in purified form.

4. The ganglioside derivative according to claim 3, wherein the basic natural ganglioside contains an oligosaccharide formed by a maximum of 4 hexose or N-acetylhexosamine residues, with at least one hexose residue present, and this saccharide part being unitary.

5. The ganglioside derivative according to claim 4, wherein the ganglioside is selected from the group consisting of gangliosides GM$_4$, GM$_3$, GM$_2$, GM$_1$-GlcNAc, GD$_2$, GD$_{1a}$-GalNAc, and GT$_{1c}$.

6. The ganglioside derivative according to claim 4, wherein the ganglioside is selected from the group consisting of gangliosides GM$_1$, GD$_{1a}$, GD$_{1b}$ and GT$_{1b}$.

7. The ganglioside derivative according to claim 1, wherein the basic semisynthetic ganglioside is an N-acyl-N-lyso-ganglioside wherein the acyl group is derived from an optionally substituted aliphatic acid with 1–24 carbon atoms.

8. The ganglioside derivative according to claim 7, wherein the acyl group is derived from a higher aliphatic acid with 12–22 carbon atoms.

9. The ganglioside derivative according to claim 8 wherein the acyl group is derived from palmitic acid, stearic acid, lauric acid, myristic acid or from a corresponding unsaturated acid.

10. The ganglioside derivative according to claim 7, wherein the acyl group is derived from an aliphatic carboxylic acid with 2–10 carbon atoms.

11. The ganglioside derivative according to claim 1, wherein the basic semisynthetic ganglioside is an N'-acyl-N'-lyso-ganglioside wherein the N'-acyl group is derived from an aliphatic acid with 1–24 carbon atoms.

12. The ganglioside derivative according to claim 11, wherein the acyl group is derived from an optionally substituted higher aliphatic acid with 12–22 carbon atoms.

13. The ganglioside derivative according to claim 12 wherein the acyl group is derived from palmitic acid, stearic acid, lauric acid, myristic acid or from a corresponding unsaturated acid.

14. The ganglioside derivative according to claim 11 wherein the acyl group is derived from an aliphatic carboxylic acid with 2–10 carbon atoms.

15. The ganglioside derivative according to claim 2 wherein when the semisynthetic ganglioside is an N-acyl-N-lyso-ganglioside or an N'-acyl-N'-lyso-ganglioside, the acyl group is substituted by 2 polar units, said polar units being identical or different.

16. The ganglioside derivative according to claim 15, wherein the polar units are selected from the group consisting of chlorine, bromine and fluorine atoms, free hydroxyl groups, esterified or etherified hydroxyl groups, free amino groups and mono- or dialkylated amino groups.

17. The ganglioside derivative according to claim 1, wherein the basic semisynthetic ganglioside is an N,N'- diacyl-N,N'-di-lyso-ganglioside wherein the acyl groups are derived from identical or different, optionally substituted aliphatic acids with 1–24 carbon atoms.

18. The ganglioside derivative according to claim 17, wherein at least one of the acyl groups is derived from a higher aliphatic acid with 12–22 carbon atoms.

19. The ganglioside derivative according to claim 18 wherein at least one of the acyl groups is derived from palmitic acid, stearic acid, lauric acid, myristic acid or from a corresponding unsaturated acid.

20. The ganglioside derivative according to claim 17 wherein at least one of the acyl groups is derived from an aliphatic acid with 2–10 carbon atoms.

21. The ganglioside derivative according to claim 17 wherein at least one of the aliphatic acids is substituted with 2 polar units.

22. The ganglioside derivative according to claim 1, wherein the aliphatic amino acid has a carboxylic acid function and a maximum of 22 carbon atoms.

23. The ganglioside derivative according to claim 22, wherein the amino function in the aliphatic amino acid is primary or secondary.

24. The ganglioside derivative according to claim 1, wherein the aliphatic amino acid is a naturally occurring L-amino acid.

25. The ganglioside derivative according to claim 1, wherein the amino acid is selected from the group consisting of glycine, alanine, serine, cysteine, cystine, valine, nor-valine, leucine, isoleucine, phenylalanine, tyrosine, diiodotyrosine, tryptophan, histidine, α-aminobutyric acid, methionine, nor-leucine, arginine, ornithine, lysine, aspartic acid, asparagine, glutamic acid, oxyglutamic acid, glutamine, dioxyphenylalanine, threonine and γ-aminobutyric acid.

26. The ganglioside derivative according to claim 1, wherein the aliphatic amino acid has a sulfonic acid function.

27. The ganglioside derivative according to claim 26, wherein the amino acid is selected from the group consisting of taurine, cysteic and homocysteic acid.

28. The ganglioside derivative according to claim 1 wherein the amino acid is selected from the group consisting of glycine, alanine, serine, valine, leucine, α- and γ-aminobutyric acid, aspartic acid, glutaminic acid and wherein the basic ganglioside is selected from the group consisting of $GM_4$, $GM_3$, $GM_2$, $GM_1$, GlcNAc, $GD_2$, $GD_{1\alpha}$-GalNAc and $GT_{1c}$.

29. The ganglioside derivative according to claim 1, wherein the amino acid is selected from the group consisting of glycine, alanine, serine, valine, leucine, α- and γ-aminobutyric acid, aspartic and glutamic acid and wherein the basic ganglioside is selected from the group consisting of $GM_1$, $GD_{1a}$, $GD_{1b}$ and $GT_{1b}$.

30. The ganglioside derivative according to claim 1, wherein the amino acid is selected from the group consisting of glycine, alanine, serine, valine, leucine, α- and γ-aminobutyric acid, aspartic and glutamic acid and wherein the basic ganglioside is a semisynthetic ganglioside selected from the group consisting of N-acyl-N-lyso-gangliosides, N'-acyl-N'-lyso-gangliosides and N,N'-di-acyl-N,N'-di-lyso-gangliosides.

31. The ganglioside derivative according to claim 1, wherein the amino acid is selected from the group consisting of glycine, alanine, serine, valine, leucine, α- and γ-aminobutyric acid, aspartic and glutaminic acid and wherein the semisynthetic ganglioside is selected from the group consisting of N'-acyl-N'-lyso-gangliosides in which the N'-acyl groups are derived from optionally substituted aliphatic acids with 1–24 carbon atoms, preferably 12–22 carbon atoms.

32. The ganglioside derivative according to claim 1, wherein the amino acid is selected from the group consisting of glycine, alanine, serine, valine, leucine, α- and γ-aminobutyric acid, aspartic and glutamic acid and wherein the semisynthetic ganglioside is selected from the group consisting of N,N'-diacyl-N,N'-di-lyso-gangliosides in which the acyl groups are derived from identical or different, optionally substituted aliphatic acids with 1–24 carbon atoms, preferably with 12–22 carbon atoms.

33. The ganglioside derivative according to claim 1, selected from the group consisting of the glycine amide of ganglioside $GM_1$, the L-alanine amide of ganglioside $GM_1$, the L-serine amide of ganglioside $GM_1$, the γ-aminobutyric acid amide of ganglioside $GM_1$, the L-cysteine amide of ganglioside $GM_1$, the taurine amide of ganglioside $GM_1$, the cysteic acid amide of ganglioside $GM_1$, and the homocysteic acid amide of ganglioside $GM_1$.

34. The ganglioside derivative according to claim 1, selected from the group consisting of the amide of glycine of N-lauroyl-N-lyso $GM_1$, the amide of glycine of N-stearoyl-N-lyso $GM_1$, the amide of L-alanine of N-oleyl-N-lyso $GM_1$, the amide of L-alanine of N-palmitoyl-N-lyso $GM_1$, the amide of L-serine of N-acetyl-N-lyso $GM_1$, the amide of γ-aminobutyric acid of N-propionyl-N-lyso $GM_1$, the amide of L-cysteine of N-valeryl-N-lyso $GM_1$, the amide of glycine of N'-lauroyl-N'-lyso $GM_1$, the amide of glycine of N'-stearoyl-N'-lyso $GM_1$, the amide of L-alanine of N'-oleyl-N'-lyso $GM_1$, the amide of L-alanine of N'-palmitoyl-N'-lyso $GM_1$, the amide of L-serine of N'-acetyl-N'-lyso $GM_1$, the amide of γ-aminobutyric acid of N'-propionyl-N'-lyso $GM_1$, the amide of L-cysteine of N'-valeryl-N'-lyso $GM_1$, the amide of glycine of N,N'-dilauroyl-N,N'-di-lyso $GM_1$, the amide of glycine of N,N'-distearoyl-N,N'-di-lyso $GM_1$, the amide of L-alanine of N,N'-dioleyl-N,N'-di-lyso $GM_1$, the amide of L-alanine of N,N'-dipalmitoyl-N,N'-di-lyso $GM_1$, the amide of L-serine of N,N'-diacetyl-N,N'-di-lyso $GM_1$, the amide of γ-aminobutyric acid of N,N'-dipropionyl-N,N'-di-lyso $GM_1$, and the amide of L-cysteine of N,N'-divaleryl-N,N'-di-lyso $GM_1$.

35. The ganglioside derivative according to claim 1, selected from the group consisting of the amide of taurine of N-acetyl-N-lyso $GM_1$, the amide of taurine of N'-lauryl-N'-lyso $GM_1$, the amide of taurine of N,N'-dioleyl-N,N'-di-lyso $GM_1$, the amide of cysteic acid of N-propionyl-N-lyso $GM_1$, the amide of cysteic acid of N'-stearoyl-N'-lyso $GM_1$, and the amide of cysteic acid of N,N'-divaleryl-N,N'-di-lyso $GM_1$.

36. Therapeutically acceptable salts of the compounds of claim 1.

37. Salts according to claim 36 selected from the group consisting of metal salts, alkaline metal salts, alkaline earth metal salts and organic base salts.

38. Salts according to claim 36 selected from the group consisting of acid addition salts.

39. Salts according to claim 38, selected from the group of salts prepared from inorganic acids.

40. Ganglioside derivatives according to claim 1 for their use in therapy.

41. A pharmaceutical preparation comprising, as active ingredient, a ganglioside derivative consisting of a natural or semisynthetic ganglioside, the carboxyl group in the sialic part of said natural or semisynthetic ganglioside being converted into a carboxylamide with an aliphatic amino acid or amino sulfonic acid, or a salt thereof with metals or organic bases on free carboxy or sulfonic groups or acid addition salts on any free amino groups, together with a therapeutically inert excipient.

42. Pharmaceutical preparations according to claim 41 wherein the natural ganglioside is obtained from tissues and organs of the nervous system in purified form.

43. Pharmaceutical preparations according to claim 42 wherein the semisynthetic ganglioside is chosen from the group consisting of N-acyl-N-lyso-gangliosides, N'-acyl-N'-lyso-gangliosides and N,N'-diacyl-N,N'-di-lyso-gangliosides in which the N- and N'-acyl groups are the same or different and each is a moiety of an optionally substituted acid.

44. The ganglioside derivative according to claim 1 which is the glycinamide of the natural ganglioside $GM_1$ or a salt thereof.

* * * * *